US 6,867,303 B2

(12) United States Patent
Grela

(10) Patent No.: US 6,867,303 B2
(45) Date of Patent: Mar. 15, 2005

(54) RUTHENIUM COMPLEXES AS (PRE) CATALYSTS FOR METATHESIS REACTIONS

(75) Inventor: Karol Grela, Warsaw (PL)

(73) Assignee: Boehringer Ingelheim International GmbH, Ingelheim (DE)

(*) Notice: Subject to any disclaimer, the term of this patent is extended or adjusted under 35 U.S.C. 154(b) by 0 days.

(21) Appl. No.: 10/684,996

(22) Filed: Oct. 14, 2003

(65) Prior Publication Data

US 2004/0127350 A1 Jul. 1, 2004

Related U.S. Application Data

(60) Provisional application No. 60/428,072, filed on Nov. 21, 2002.

(30) Foreign Application Priority Data

Oct. 15, 2002 (PL) ................................. 356652

(51) Int. Cl.[7] ............................. C07F 15/00; C07F 9/02; B01J 31/00
(52) U.S. Cl. ....................... 548/101; 548/262.2; 556/21; 556/22; 556/136; 502/152; 502/162; 502/167
(58) Field of Search ............................ 556/21, 22, 136; 548/101, 262.2; 502/152, 162, 167

(56) References Cited

FOREIGN PATENT DOCUMENTS

WO    WO 02/14376 A2    2/2002

OTHER PUBLICATIONS

Kalanderopoulos et al., J. Am. Chem. Soc., vol. 108, No. 20, pp. 6290–6265 (1986).*
S. Gessler, et al. "Synthesis and Metathesis Reactions of a Phosphine–free Dihydroimidazole Carbene Ruthenium Complex", Tetra. Lett. 41 (2000) 9973–9976.
S. Garber, et al. "Efficient and Recyclable Monomeric and Dendritic Ru–Based Metathesis Catalysts", J. Am. Chem. Soc. 2000, 122, 8168–8179.
H. Wakamatsu, et al. "Ein hochaktiver und luftstabiler Rutheniumkomplex für die Olefinmetathese", Angew. Chem. 2002, 114 Nr. 5. 832–834.
H. Wakamatsu, et al. "A New Highly Efficient Ruthenium Metathesis Catalyst", Angew. Chem. 2002, 114, Nr. 13, 2509–2511.

* cited by examiner

Primary Examiner—Porfirio Nazario-Gonzalez
(74) Attorney, Agent, or Firm—Michael P. Morris; Mary-Ellen M. Devlin; Philip I. Datlow

(57) ABSTRACT

The invention relates to new (pre)catalysts of ruthenium complexes of formula 1,

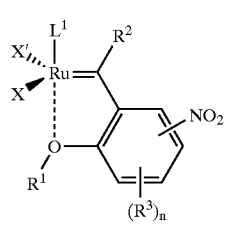

wherein $L^1$, X, X', $R^1$, $R^2$, $R^3$ and n are defined herein. The novel ruthenium complexes of formula 1 are convenient (pre)catalysts for metathesis reactions and can be applied, e.g., for ring-closing metathesis, cross metathesis or ene-ine metathesis reactions. Another aspect of the invention are the novel intermediates of formula 2.

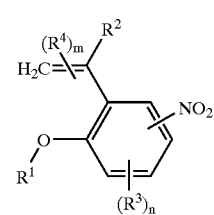

21 Claims, 1 Drawing Sheet

RUTHENIUM COMPLEXES AS (PRE) CATALYSTS FOR METATHESIS REACTIONS

RELATED APPLICATIONS

Benefit of U.S. Provisional Application Ser. No. 60/428,072, filed on Nov. 21, 2002 is hereby claimed, and said application is herein incorporated by reference in its entirety.

BACKGROUND OF THE INVENTION

1. Technical Field

This invention relates to ruthenium carbene complexes of formula 1, their synthesis and their practical use as catalysts for different types of metathesis reactions.

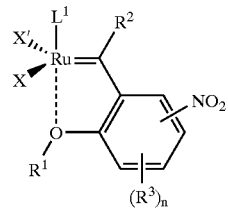

1

2. Background Information

Great progress has been made in the last few years in the application of olefins metathesis in organic synthesis. Some ruthenium carbene complexes acting as (pre)catalysts have been developed, which possess a high activity in various metathesis reactions as well as a broad tolerance for a number of functional groups. This combination of characteristics is a basis for the usability of such (pre)catalysts in organic synthesis.

Moreover, for the practical application, especially in industrial scale, it is very desirable that these ruthenium complexes are stable for a longer period of time in the conditions of thermal load and that they can be stored, purified and applied without the atmosphere of protective gases.

Ruthenium complexes with the above mentioned characteristics are known in literature. See J. Am. Chem. Soc. 2000, 122, 8168–8179 or Tetrahedron Lett. 2000, 41, 9973–9976. However, it has been discovered that a better stability is connected with a lower catalytic activity. Such a limitation was found for example for the (pre)catalyst of the formula A (see Angew. Chemie Int. Ed. 2002, 114, 832).

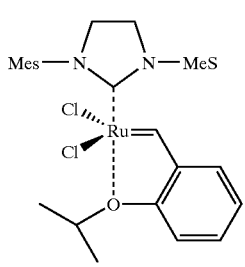

A

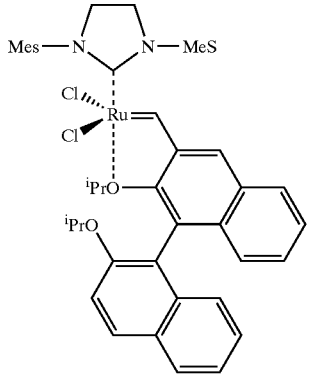

B

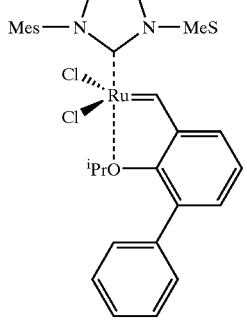

C

Next, (pre)catalysts of the formula B and C were described, which demonstrate a higher catalytic activity in comparison with the (pre)catalyst of the formula A. The catalysts A, B and C contain an iso-propoxy group chelating the metal atom. The reason for a higher activity of the systems B and C is a steric hindrance caused by the presence of a phenyl or a (substituted) naphthyl group in ortho-position to the iso-propoxy group (Angew. Chemie Int. Ed. 2002, 114, 832–834; Angew. Chemie Int. Ed. 2002, 114, 2509–2511).

It has been found surprisingly that ruthenium complex (pre)catalysts of general formula 1, containing an aromatic nitro group, demonstrate much higher catalytic activity in comparison to known highly active ruthenium complexes and that these complexes are at the same time thermal and air stable.

BRIEF-SUMMARY OF THE INVENTION

The present invention relates to novel ruthenium complexes of formula 1, their synthesis, the synthesis of all intermediates and the use of complexes of formula 1 as catalysts or as precatalysts,

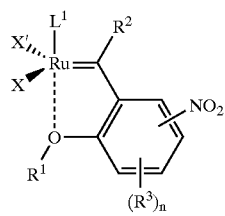

1 wherein $L^1$ is a neutral ligand;

X and X' are anionic ligands;

$R^1$ is —$C_{1-5}$-alkyl or —$C_{5-6}$-cycloalkyl;

$R^2$ is H, —$C_{1-20}$-alkyl, —$C_{2-20}$-alkenyl, —$C_{2-20}$-alkynyl or aryl;

$R^3$ is —$C_{1-6}$-alkyl, —$C_{1-6}$-alkoxy or aryl, wherein aryl may be substituted with —$C_{1-6}$-alkyl or —$C_{1-6}$-alkoxy;

n is 0, 1, 2 or 3.

The compounds of formula 1 of the present invention may be used to catalyse olefin metathesis reactions including, but not limited to, ring opening metathesis polymerisation (ROMP), ring closing metathesis (RCM), depolymerisation of unsaturated polymers, synthesis of telechelic polymers, ene-ine metathesis and olefin synthesis.

Another embodiment of the present invention relates to novel 2-alkoxy-5-nitrostyrene derivatives of formula 2, which are intermediates for the preparation of complexes 1,

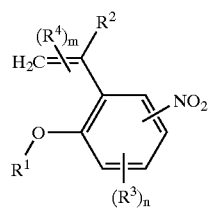

2 wherein $R^1$, $R^2$, $R^3$ and n are defined as above and $R^4$ is —$C_{1-20}$-alkyl;

m is 0, 1 or 2;

the partial formula

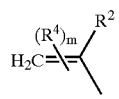

represents an alkylene group in which one or both hydrogen atoms of the methylene group may be replaced by the group $R^4$. Accordingly it covers the following alkylene groups:

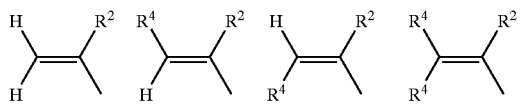

A further aspect of the invention is the preparation of novel 2-alkoxy-5-nitrostyrene derivatives of formula 2, wherein:

A substituted 2-hydroxy-5-nitrobenzaldehyde 3 is alkylated by a $R^1Z$, wherein $R^1$ has the meaning given for formula 1 and Z is a leaving group selected from halogen atoms, $C_{1-6}$-alkyl-S(O)—O—, $C_{1-6}$-fluoroalkyl-S(O)—O—, aryl-S(O)—O— or aryl-S(O)$_2$—O—.

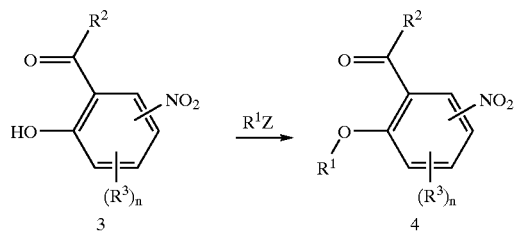

The substituted 2-alkoxy-5-nitrobenzaldehyde of formula 4 is then treated with an olefination reagent of formula

wherein $R^4$ and m has the meaning given for formula 2 and W is a leaving group suitable for olefination reactions; to yield formula 2,

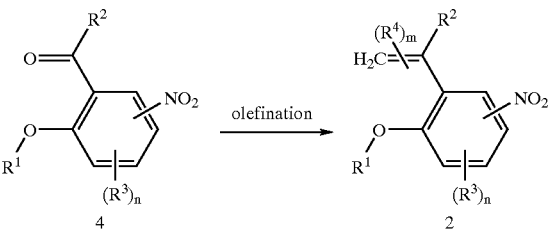

Compound 2 can then be reacted with a ruthenium complex of formula 5 in which $L^1$ and $L^2$ are neutral ligands; $R^5$ is H, —$C_{1-20}$-alkyl, —$C_{2-20}$-alkenyl, —$C_{2-20}$-alkynyl or aryl; $R^6$ is aryl, vinyl or allenyl and X and X' are anionic ligands, to result in the ruthenium complex of the formula 1.

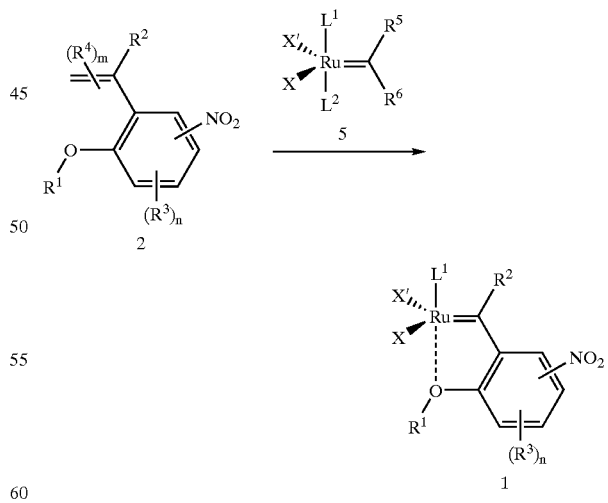

Optionally, the obtained compound of formula 1 can then be reacted with a different neutral ligand $L^1$ to replace the neutral ligand $L^1$ that is present in the compound of formula 1 and thereby obtain a different compound of formula 1.

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins can also be present in the compounds described herein, and all such stable isomers are contemplated in the present invention. Cis and Trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

DETAILED DESCRIPTION OF THE INVENTION

Figure 1:
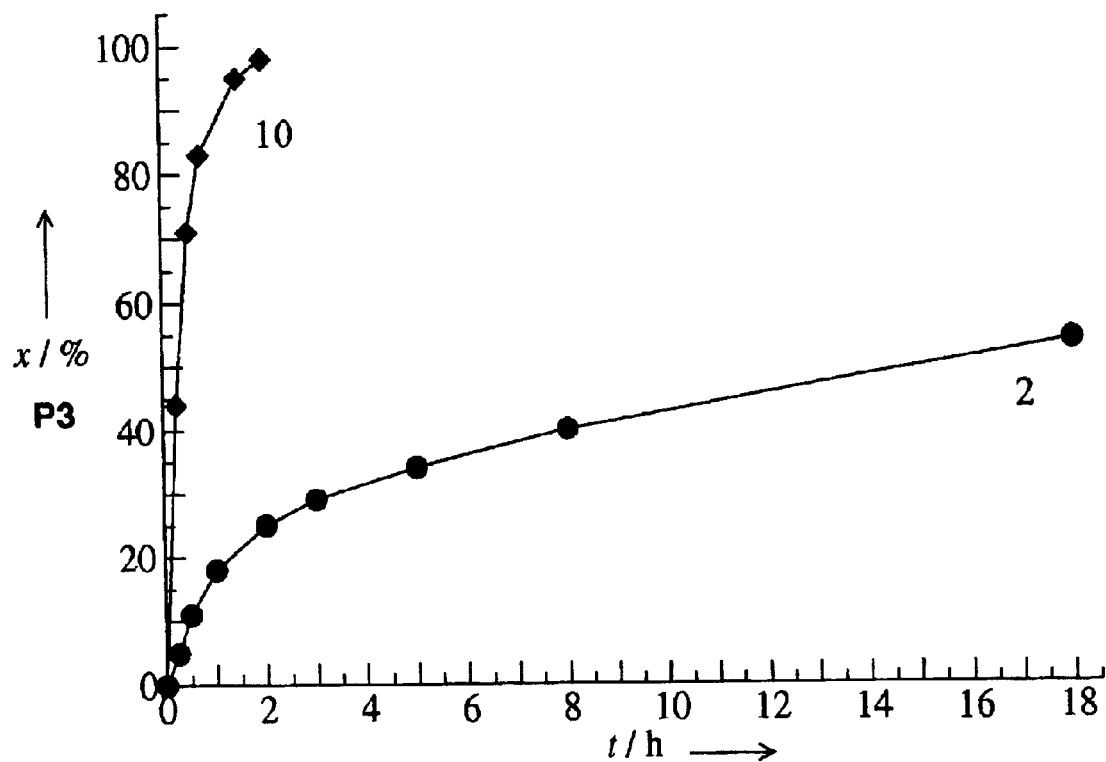
FIG. 1 is a graph comparing the cyclization speed of 2-allyl-2-(2-methylallyl)diethyl malonate when using a ruthenium catalyst according to the present invention versus using a known ruthenium catalyst.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —$C_{1-6}$ alkyl means an alkyl group or radical having 1 to 6 carbon atoms. Unless otherwise specified below, conventional definitions of terms control and conventional stable atom valences are presumed and achieved in all formulas and groups.

The term "substituted" as used herein, means that any one or more hydrogens on the designated atom is replaced with a selection from the indicated group, provided that the designated atom's normal valence is not exceeded, and that the substitution results in a stable compound.

The term "aryl" as used herein, either alone or in combination with another substituent, means either an aromatic monocarbocyclic system or aromatic multicarbocyclic systems. For example, aryl includes a phenyl or a naphthyl ring system.

The term "halogen" as used herein means a halogen substituent selected from fluoro, chloro, bromo or iodo.

The term "—$C_{1-20}$-alkyl" as used herein, either alone or in combination with another substituent, means acyclic, straight or branched chain alkyl substituents containing from one to twenty carbon atoms. The terms "—$C_{1-5}$-alkyl" or "—$C_{1-6}$-alkyl" as used herein have the same meaning as the above mentioned term but contains less carbon atoms, precisely a maximum of five or six carbon atoms. The terms —$C_{1-20}$-alkyl, —$C_{1-5}$-alkyl or —$C_{1-6}$-alkyl can include i.e. methyl, ethyl, propyl, butyl, hexyl, 1-methylethyl, 1-methylpropyl, 2-methylpropyl or 1,1-dimethylethyl.

The term "—$C_{2-20}$-alkenyl" as used herein, either alone or in combination with another substituent, means acyclic, straight or branched chain alkenyl substituents containing from two to twenty carbon atoms and at least one double bond. The term "—$C_{2-6}$-alkenyl" as used herein has the same meaning as the above mentioned term but contains less carbon atoms, precisely a maximum of six carbon atoms. The terms —$C_{1-20}$-alkenyl or —$C_{1-6}$-alkenyl can include i.e. vinyl or allenyl.

The term "—$C_{2-20}$-alkynyl" as used herein, either alone or in combination with another substituent, means acyclic, straight or branched chain alkynyl substituents containing from two to twenty carbon atoms and at least one triple bond. The term "—$C_{2-6}$-alkynyl" as used herein has the same meaning then the above mentioned term but contains less carbon atoms, precisely a maximum of six carbon atoms.

The term "—$C_{5-6}$-cycloalkyl" as used herein, either alone or in combination with another substituent, means a cycloalkyl substituent containing five or six carbon atoms and includes i.e. cyclopentyl or cyclohexyl.

The term "—$C_{1-6}$-alkoxy" as used herein, either alone or in combination with another substituent, means the substituent —$C_{1-6}$-alkyl-O— wherein alkyl is as defined above containing up to six carbon atoms. Alkoxy includes methoxy, ethoxy, propoxy, 1-methyl-ethoxy, butoxy or 1,1-dimethylethoxy.

Additional Embodiments

Preferred are compounds of formula 1a, wherein $L^1$, X, X', $R^1$, $R^2$, $R^3$ and n are defined as above.

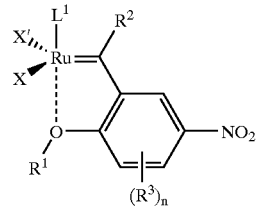

1a

More preferred are compounds of general formula 1 or 1a wherein $L^1$ is $P(R^{11})_3$ and $R^{11}$ are each independantly —$C_{1-6}$-alkyl, —$C_{3-8}$-cycloalkyl or aryl; or $L^1$ is a ligand of formula 6a, 6b, 6c or 6d,

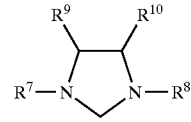

6a

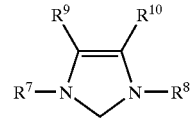

6b

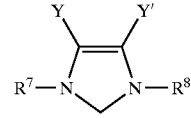

6c

-continued

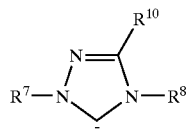
6d wherein
R[7] and R[8] are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen; particularly R[9] and R[10] are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen or R[9] and R[10] together with the carbon atoms to which they are attached are combined to form a carbocyclic 3 to 8 membered ring.

Y and Y' are halogen.

Particularly preferred are compounds wherein
R[7] and R[8] are each independently H, —$C_{1-6}$-alkyl, —$C_{2-6}$-alkenyl or phenyl, wherein the phenyl is optionally substituted with up to three groups independently selected from —$C_{1-6}$-alkyl, —$C_{1-6}$-alkoxy or halogen;

R[9] and R[10] are each independently H, —$C_{1-6}$-alkyl, —$C_{2-6}$-alkenyl or phenyl, wherein the phenyl is optionally substituted with up to three groups independently selected from —$C_{1-6}$-alkyl, —$C_{1-6}$-alkoxy or halogen or R[9] and R[10] together with the carbon atoms to which they are attached are combined to form a carbocyclic 5 to 7 membered ring.

Most preferred are compounds of general formula 1 or 1a, wherein
R[1] is a iso-propyl group; and/or
R[2] is H, —$C_{1-6}$-alkyl or aryl, in particular R[2] has the meaning of a hydrogen atom; and/or
X and X' are halogen, particularly chlorine; and/or
L[1] is P(cyclohexyl)$_3$; or
L[1] is a group of formula 6a, 6b, 6c or 6d; and/or
R[7] and R[8] are 2-methylbenzene, 2,6-dimethylbenzene or 2,4,6-trimethylbenzene; and/or
n is 0.

Additional embodiments are compounds of formula 1 or 1a wherein:
R[1] is iso-propyl;
R[2] is H;
n is 0;
X and X' are each chlorine; and
L[1] is a ligand of formula 6a:

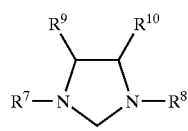
6a wherein R[7] and R[8] are each 2,4,6-trimethylphenyl; and R[9] and R[10] are each H.

Preferred are compounds of formula 2a, wherein R[1], R[2], R[3], R[4], m and n are defined as above.

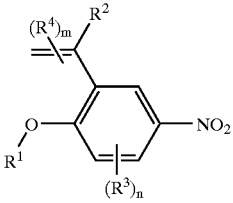
2a

More preferred are compounds of general formula 2 or 2a, wherein
R[1] is a iso-propyl group; and/or
R[2] is H, —$C_{1-6}$-alkyl or aryl, in particular R[2] has the meaning of a hydrogen atom; and/or
R[4] is —$C_{1-6}$-alkyl, in particular methyl or ethyl; and/or
n is 0 and/or
m is 0.

Additional embodiments are compounds of formula 2 or 2a wherein:
R[1] is iso-propyl;
R[2] is H;
m is 0; and
n is 0.

Furthermore preferred is a process for manufacturing complexes of formula 1 or 1a, wherein a compound of general formula 2 or 2a, is reacted with a ruthenium complex of formula 5

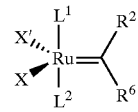
5 wherein
L[1] and L[2] are neutral ligands
R[5] is H, —$C_{1-20}$-alkyl, —$C_{2-20}$-alkenyl, —$C_{2-20}$-alkynyl or aryl; and
R[6] is aryl, vinyl or allenyl; and
X and X' are anionic ligands; optionally in the presence of a different neutral ligand L[1].

More preferred is the above mentioned synthesis of a ruthenium complex of formula 1, when the process is carried out:
in the presence of a copper salt, in particular CuCl; and/or
in a halogenated or an aromatic solvent, particularly selected from methylene chloride, chloroform, benzene, toluene, xylene, mesitylen or mixtures thereof; and/or
at a temperature from 0 to 100° C., in particular at a temperature from 10 to 80° C., more particular at a temperature from 20 to 60° C.; and/or
in a time period from 1 to 24 h, in particular 1 to 10 h, more particular 1 to 4 h.

Most preferred is the above mentioned synthesis of a ruthenium complex, wherein the reaction is carried out in one vessel by mixing the ligand of formula 6a, 6b, 6c or 6d with a solid complex of formula 5, wherein both ligands L[1] and L[2] are phosphines of formula P(R[11])$_3$, wherein R[11] has the meaning as above and thereafter adding a ligand of formula 2 or 2a.

One preferred variation of the above mentioned synthesis of a ruthenium complex is the generation of the ligands of general formula 6a, 6b, 6c or 6d in situ from the stable salts of the formulae 7a, 7b, 7c or 7d,

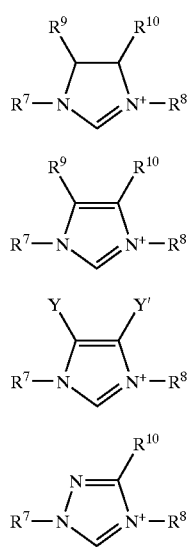

wherein the anion is selected from formate, acetate, triflouro-acetate or another acid group, a halogen or $[BF_4]^-$. Therefore, the salt is preferably in form of a suspension in solvents such as aliphatic or aromatic hydrocarbons, preferably hexane, and reacted with a strong base, selected from alkali metal hydrides, alkaline earth metal hydrides or alcoholates, particularly potassium tert-pentanolate, potassium tert-amylate or potassium tert-butanolate. Thereafter, the reaction is continued by adding a solid complex of formula 5, wherein both ligands $L^1$ and $L^2$ are phosphines of formula $P(R^{11})_3$ and thereafter adding a ligand of formula 2 or 2a, to yield a compound of general formula 1 or 1a.

Moreover preferred is a process for manufacturing intermediates, which comprises the steps of a) alkylating a compound of general formula 3, with a reagent of formula $R^1Z$ (9) to form a intermediate of formula 4, and b) reacting 4 with an olefination reagent of formula 10 to yield a compound of the general formula 2,

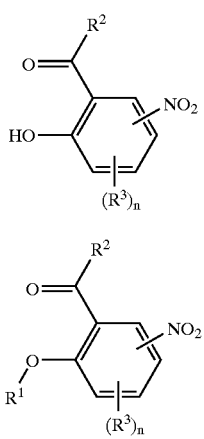

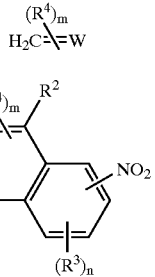

wherein $R^1$, $R^2$, $R^3$, $R^4$, m and n of formula 2a, 3, 4, 9 and 10 are defined as above and W is a leaving group suitable for olefination reactions; and.

Z is halogen, —$C_{1-6}$-alkyl-S(O)—O—, —$C_{1-6}$-fluoroalkyl-S(O)—O—, aryl-S(O)—O— or aryl-S(O)$_2$—O—.

More preferred is a process, wherein the above mentioned step a) is carried out:

in an aprotic solvent, in particular selected from DMF, DMSO, acetone, acetonitrile, ethyl acetate, glycol ether, methanol, ethanol or mixtures thereof, more particular the solvent is DMF; or in a biphasic solvent system fitted with a phase transfer catalyst; or in presence of a catalyst, in particular the catalyst is selected from $Cs_2CO_2$, CsF, quaternary ammonium salts, crown ethers or cryptands, more particular $Cs_2CO_3$; or in the presence of an alkali metal carbonate or an alkali hydroxide, in particular selected from $Na_2CO_3$, $K_2CO_3$, $Li_2CO_3$, $Cs_2CO_3$, NaOH, KOH, LiOH, CsOH; or in a time period from 1 to 24 h, in particular 8 to 24 h, more particular 16 to 24 h.

at a temperature from 0 to 150° C., in particular at a temperature from 10 to 100° C., more particular at a temperature from 20 to 80° C.; or Starting from compound 4, compound 2 is available under Tebbe, Wittig, Wittig-Horner, Wittig-Horner-Emmons or Peterson conditions, but preferred is a process, wherein the above mentioned step b) is carried out:

in a solvent selected from alcohols, glycol ethers or cyclic ethers, preferred is THF; or W is a leaving group suitable for olefination reactions according to Tebbe, with Tebbe's titanium reagent, or according to Wittig, with Wittig's phosphonium ylide reagent, more particular a leaving group selected from $PPh_3$ or $TiCp_2$; wherein Ph is substituted or unsubstituted phenyl and Cp is a substituted or unsubstituted cyclopentadienyl-anion, which can be found after reaction in its oxidised form.

Another preferred embodiment of the invention is a process for metathesis reactions of all types, comprising contacting an olefin with a catalyst of general formula 1 or 1a; in particular wherein the metathesis reaction is a ring closing or cross metathesis reaction.

The following examples are to illustrate various embodiments of the present invention and are not to be understood as limiting the present invention in a way.

EXAMPLE 1

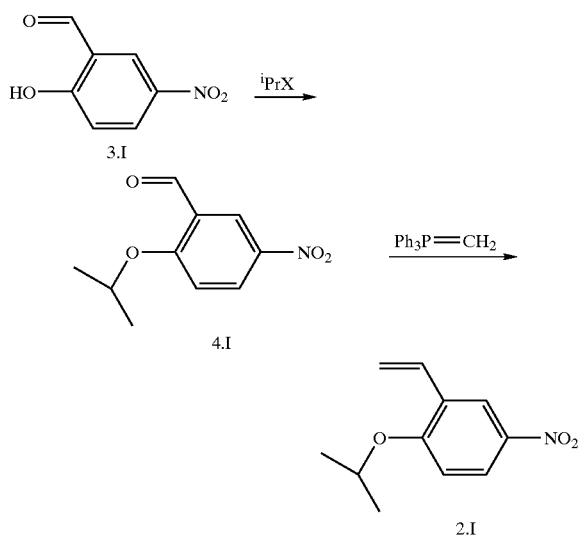

4.I: To a stirred suspension of powdered anhydrous potassium carbonate (1.1 g, 8 mmol), a catalytic amount of caesium carbonate (521 mg, 40 mol %) and 3.I (668 mg, 4 mmol) in dry DMF (25 ml) was added neat 2-iodopropane (0.8 ml, 8 mmol). The reacting mixture was stirred for 24 h at room temperature (RT), and then the solvent was evaporated in vacuum. The residue was poured to water (50 ml) and extracted with $^t$BuOMe (4×25 ml). The combined organic layers were washed with brine, dried with $Mg_2SO_4$ and evaporated to dryness. Crude product was purified using silica-gel column chromatography (cyclohexane/EtOAc 8:2), to give 2-iso-propoxy-5-nitrobenzaldehyde 4.I as low-melting solid (850 mg, 86% of yield).

IR (KBr): ν[cm$^{-1}$]=3115, 2991, 2942, 1679, 1609, 1526, 1348, 1284, 1111, 950, 832, 748, 667; $^1$H-NMR (500 MHz, CDCl$_3$): δ[ppm]=1.48(d, 6H, J=6.1 Hz), 4.85 (q, 1H, J=6.1 Hz), 7.10 (d, 1H, J=9.2 Hz), 8.39 (dd, 1H, J=2.9, 9.2 Hz), 8.69 (d, 1H, J=2.9 Hz), 10.41 (s, 1H); $^{13}$C-NMR (125 MHz, CDCl$_3$): δ[ppm]=21.8, 72.6, 113.6, 124.7, 125.12, 130.4, 141.1, 164.3, 187.8; MS (EI): m/z 209 (10, [M]+.), 167 (100), 137 (18), 120 (11), 93 (7), 75 (3), 65 (10), 53 (4); HRMS (EI) calculated for [M]+($C_{10}H_{11}O_4N$): 209.0688; found 209.0686.

2.I: To a stirred suspension of Ph$_3$PCH$_3$Br (932 mg, 2.53 mmol) in dry THF (20 ml) was added slowly at −78° C. successive a solution of BuLi in hexane (1.8 ml, 2.7 mmol, 1.5M) and a solution of 4. I in dry THF (2 ml). After this the reaction mixture was allowed to warm to r.t. and was stirred for additional 10 h. After this time a saturated solution of NH$_4$Cl (2 ml) and $^t$BuOMe (100 ml) were added. Insoluble material was filtered-off and the resulting solution evaporated in vacuum. Crude product was purified by column chromatography on silica-gel (using cyclohexane/EtOAc 8:2) to give 2-iso-propoxy-5-nitrostyrene 2.I as pale yellow oil (236 mg, 63% of yield).

IR (film): ν[cm$^{-1}$]=3088, 2982, 2967, 1627, 1607, 1583, 1516, 1341, 1271, 1107, 950, 742 cm-1; $^1$H-NMR (500 MHz, CDCl$_3$): δ[ppm]=1.41 (d, 6H, J=6.0 Hz), 4.71 (q, 1H, J=6.0 Hz), 5.40 (dd, 1H, J=0.5, 11.2 Hz), 5.87 (dd, 1H, J=0.5, 17.7 Hz), 6.91 (d, 1H, J=9.1 Hz), 7.00 (dd, 1H, J=11.2, 17.7 Hz), 8.12 (dd, 1H, J=2.8, 9.1 Hz), 8.36 (d, 1H, J=2.8 Hz); $^{13}$C-NMR (125 MHz, CDCl$_3$): δ[ppm]=21.9, 71.5, 112.2, 116.8, 122.4, 124.5, 128.1, 130.1, 141.0, 159.9; MS (EI): m/z 207 (4, [M]+.), 165 (59), 148 (100), 135 (4), 118 (96), 104 (2), 90 (15), 65 (8), 63 (7), 51 (4); MS (ESI): m/z 230 ([M+Na]+); HRMS (ESI): m/z calculated for [M+Na]+($C_{11}H_{13}O_3NNa$): 230.0788; found 230.0776.

EXAMPLE 2

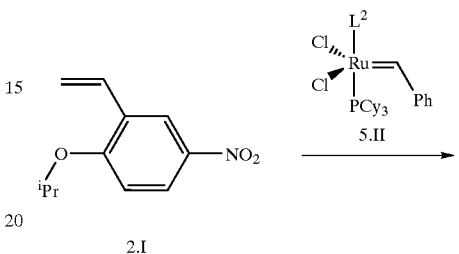

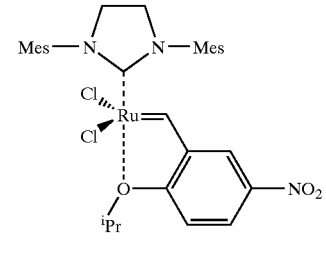

Under an argon atmosphere a carbene complex of formula 5.II, wherein $L^2$ represents a NHC ligand of formula 6a.II (153 mg, 0.18 mmol),

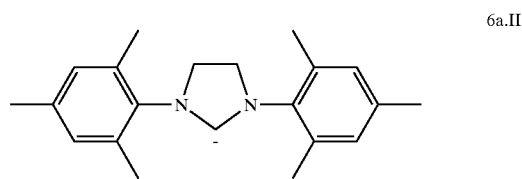

and anhydrous CuCl (18 mg, 0.18 mmol) were placed in a Schlenck tube. Then dry, deoxygenated CH$_2$Cl$_2$ (10 ml) was added followed by a solution of compound 2.I (38 mg, 0.18 mmol) in CH$_2$Cl$_2$ (4 ml). The resulting suspension was stirred at 30° C. for 1 h, thereafter it was concentrated in vacuum, and purified by silica-gel column chromatography (cyclohexane/EtOAc 5:2). After removal of solvent and washing with small amount of dry n-pentane complex 1.II, wherein Mes has the meaning of a mesityl group, was obtained as green, microcrystalline solid (100 mg, 83% of yield). R$^f$=0.30 (hexane/EtOAc 8:2);

$^1$H-NMR (500 MHz, CD$_2$Cl$_2$): δ[ppm]=16.42 (s, 1H), 8.46 (dd, 1H, J=9.1, 2.5 Hz), 7.80 (d, 1H, J=2.5 Hz), 7.10 (s, 4H), 6.94 (d, 1H, J=9.1 Hz), 5.01 (sept, 1H, J=6.1 Hz), 4.22 (s, 4H), 2.47 (2s, 18H), 1.30 (d, 6H, J=6.1 Hz); $^{13}$C-NMR (125 MHz, CD$_2$Cl$_2$): δ[ppm]=289.1, 208.2, 156.8, 150.3, 145.0, 143.5, 139.6, 139.3, 129.8, 124.5, 117.2, 113.3, 78.2, 52.0, 21.3, 21.2, 19.4; IR (KBr): ν[cm$^{-1}$]=2924, 2850, 1606, 1521, 1480, 1262, 1093, 918, 745; MS (ESI): m/z 636 [M−Cl]+; HRMS(EI): m/z calculated for C$_{31}$H$_{37}$N$_3$O$_3$Ru:

[M+.] 671.1255, found 671.1229; Elemental analysis, calculated: (%) for $C_{31}H_{37}N_3O_3Ru$ (671.63): C, 55.44; H, 5.55; N, 6.26; found: C, 55.35; H, 5.70; N, 6.09.

EXAMPLE 3

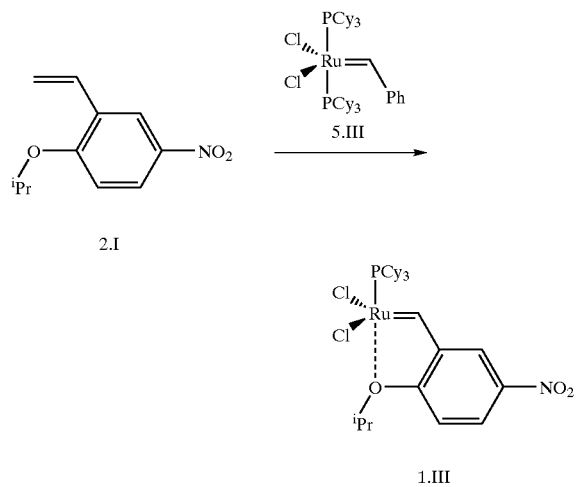

Under an argon atmosphere a carbene complex of formula 5.III (164.6 mg, 0.20 mmol) was placed in a Schlenck tube. Then dry, deoxygenated $CH_2Cl_2$ (15 ml) was added followed by a solution of compound 2.I (50 mg, 0.24 mmol) in $CH_2Cl_2$ (5 ml). The resulting suspension was stirred at 40° C. for 1 h, thereafter it was concentrated in vacuum, and purified by silica-gel column chromatography (cyclohexane/EtOAc 5:2). After removal of solvents and washing with small amount of dry n-pentane a complex 1.III was obtained as brown, microcrystalline solid (95 mg, 70% of yield).

$^1$H-NMR (500 MHz, $CDCl_3$): □[ppm]=1.26–2.35 (m, 39H), 5.33–5.40 (m 1H), 7.18 (d, J=5 Hz, 1H), 8.54 (d, J=5 Hz, 1H), 8.60 (s, 1H), 17.38 (d, J=5.0 Hz, 1H); $^{13}$C-NMR (125 MHz, $CDCl_3$): □[ppm]=22.1, 26.2, 27.7 (d, J=24 Hz), 30.1, 35.8 (d, J=10 Hz), 78.2, 113.2, 117.6, 124.2, 143.3, 157.0, 273.2; IR ($CH_2Cl_2$, film): v[cm$^{-1}$]=2930 (s), 2852 (s), 1604 (m), 1575 (m), 1521 (s), 1476 (m), 1447 (m), 1379 (w), 1342 (s), 1275 (s), 1241 (m), 1205 (w), 1181 (w), 1136 (m), 1095 (s), 1049 (w), 1005 (w), 951 (m), 918 (s), 851 (m), 830 (m), 789 (m), 745 (s), 656 (m), 606 (m), 518 (m); HRMS (EI): m/z calculated for $C_{28}H_{44}O_3N^{(35)}Cl_2P^{(102)}Ru$ (M$^+$): 645.14794; found 645.14706.

EXAMPLE 4

Salt 7.IV (152 mg, 0.388 mmol) was suspended under argon in a Schlenck tube in n-hexane (7 ml).

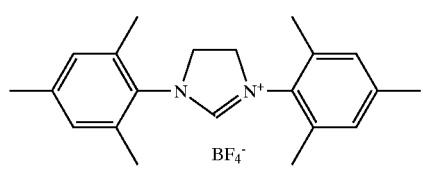

Thereafter potassium tert-amylate $CH_3CH_2C(CH_3)_2O^-K^+$ (0.22 ml, 0.372 mmol, 1.7 M solution of toluene) was added and the resulting, pale yellow turbid solution was stirred at r.t. for 30 min.

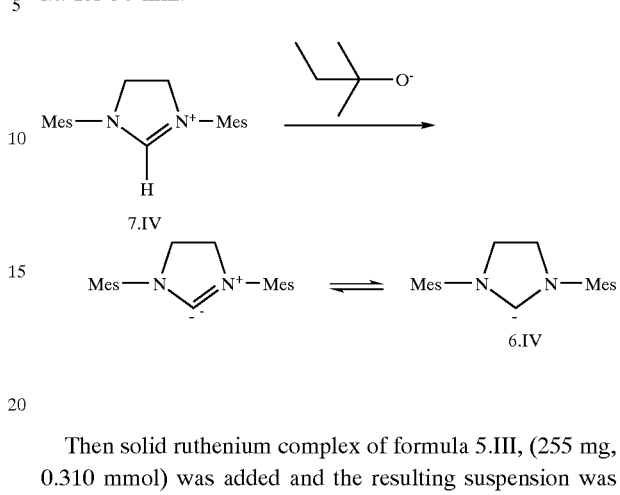

Then solid ruthenium complex of formula 5.III, (255 mg, 0.310 mmol) was added and the resulting suspension was refluxed for 30 min. To the resulting brown-pink suspension a solution of compound 2.I (83.5 mg, 0.403 mmol) in $CH_2Cl_2$ (7 ml) and solid CuCl (33.8 mg, 0.341 mmol) were added at r.t.

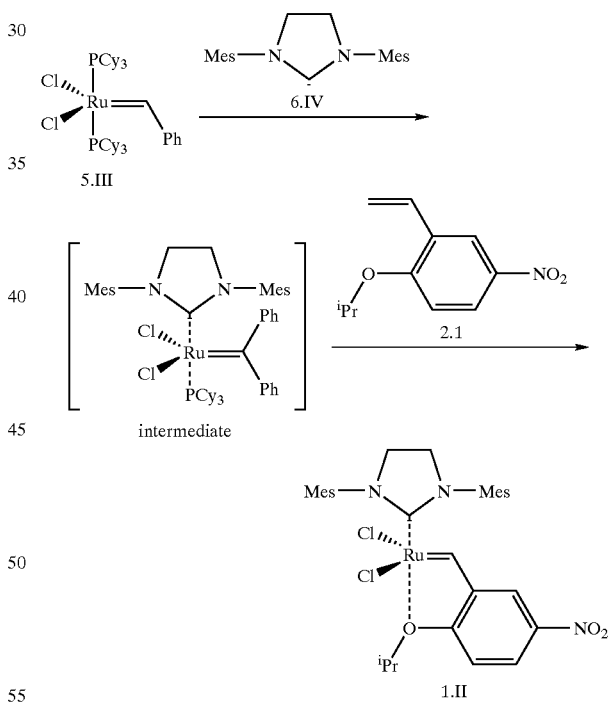

The resulting mixture was heated at 40° C. for 1 h. The resulting mixture was concentrated in vacuum, and purified by silica-gel column chromatography (cyclohexane/EtOAc 5:2). After removal of solvent and washing with small amount of dry n-pentane complex 1.II was obtained as green, microcrystalline solid (149 mg, 72% of yield). Analytical data are in agreement with those obtained previously (see Example 2).

EXAMPLE 5

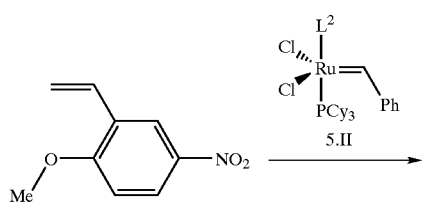

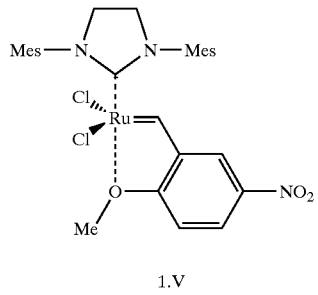

Preparation of complex 1.V analog to Example 2 results a green, microcrystalline solid (40% of yield).

IR (KBr): ν[cm$^{-1}$]=2924 (s), 2853 (s), 1608 (m), 1523 (m), 1483 (s), 1343 (s), 1267, 1010 (w), 905 (s), 826 (m), 745 (m). MS(EI): m/z 643 (3), 322 (4), 304 (100), 289 (11), 246 (5), 181 (12), 159 (12), 158 (12), 105 (8), 77 (15), 43 (58). MS (LSIMS) m/z 644 (M+H+).

Usage of a compound of general formula 1 as a catalyst for metathesis reaction, respectively the syntheses of compounds containing a double bond C=C and/or other functional groups occurs with surprisingly high success. Therefore the below described new (pre)catalysts of formula 1 appear to be better than other comparable known highly active ruthenium catalysts; especially if one concern their activity. As a consequence thereof lower amounts of the catalyst, lower reaction temperatures and lower reaction times are necessary, for better yield in comparison with the established complexes usually used. The following examples 6–10 are showing this superiority of catalysts of formula 1.

EXAMPLE 6

Ring closing metathesis reactions catalyzed by compounds of the formula 1.II (see Example 2)

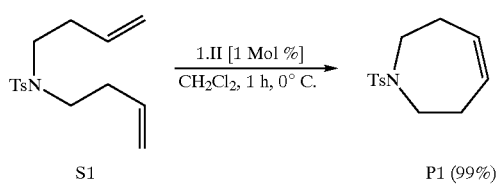

To a solution of diene S1 (210 mg, 0.75 mmol) in CH$_2$Cl$_2$ (35 ml) a solution of catalyst 1.II (5 mg, 1 mol %) in CH$_2$Cl$_2$ (2 ml) was added at 0° C. After stirring at 0° C. for an additional hour, the solvent was removed under vacuum and the residue was purified using silica-gel column chromatography (cyclohexane/EtOAc 8:2) to give P1 (186 mg, 99% of yield) as a colourless solid. IR (KBr): ν[cm$^{-1}$]=3030, 2942, 2899, 2855, 1657, 1596, 1450, 1332, 1286, 1162, 910, 816, 712; $^1$H-NMR (200 MHz, CDCl$_3$): δ[ppm]=2.28 (m, 4H), 2.39 (s, 3H), 3.25 (m, 4H), 5.72 (m, 2H), 7.25 (d, 2H, J=8.2 Hz), 7.64 (d, 2H, J=8.2 Hz); $^{13}$C-NMR (50 MHz, CDCl$_3$): δ[ppm]=21.5, 29.948.2, 126.9, 129.5, 130.1, 136.2, 142.9; MS (EI): m/z 251 (5, [M]+) 223 (2), 184 (6), 155 (4), 105 (2), 91 (19), 96 (16), 77 (1), 65 (13), 42 (100); HRMS (EI) m/z calculated for [M]+(C$_{13}$H$_{17}$O$_2$NS): 251.0980; found 2251.0979.

EXAMPLE 7

Cross metathesis reactions catalyzed by compounds of the formula 1.II (see Example 2)

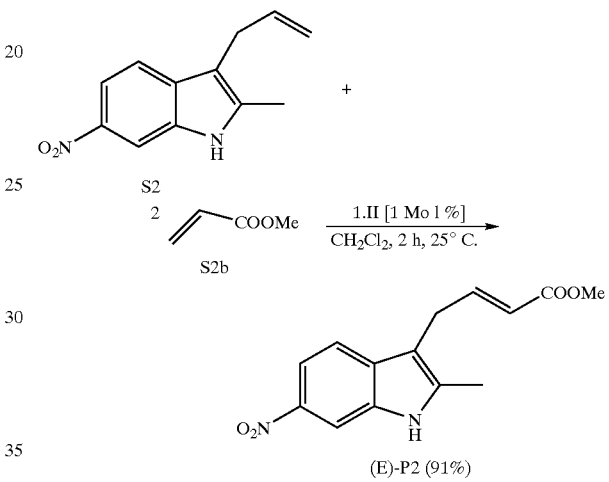

To a stirred solution of indole S2 (77.8 mg, 0.36 mol) and methyl acrylate S2b (92.9 mg, 1.1 mmol) in dry CH$_2$Cl$_2$ (15 ml) a solution of the catalyst 1.II (12.1 mg, 5 mol %) in CH$_2$Cl$_2$ (5 ml) was added. The resulted mixture was stirred at r.t. for 2 h. Solvent was removed in vacuum and the residue purified using silica-gel column chromatography (cyclohexane/EtOAc 8:2) to give (E)-P2 (186 mg, 99% of yield) as yellow crystalline solid.

IR (KBr): ν[cm$^{-1}$]=3364, 2953, 2904, 1707, 1655, 1504, 1324, 1215, 750 cm-1; $^1$H-NMR (500 MHz, CDCl$_3$): δ[ppm]=2.42 (s, 3H), 3.61 (dd, 2H, J=1.7, 6.0 Hz), 3.70 (s, 3H), 5.74 (dt, 1H, J=1.7, 15.7 Hz), 7.09 (dt, 1H, J=6.0, 15.7 Hz), 7.42 (d, 1H, J=8.8 Hz), 7.98 (dd, 1H, J=2.0, 8.8 Hz), 8.24 (d, 1H, J=2.0 Hz), 8.51 (br. s, 1H), $^{13}$C-NMR (125 MHz, CDCl$_3$): δ[ppm]=12.0, 26.7, 51.5, 107.2, 108.8, 115.4, 117.5, 121.4, 133.2, 133.6, 138.9, 142.6, 146.7, 167.0; MS (EI): m/z 274 (100, [M]+.), 259 (75), 242 (63), 215 (38), 199 (11), 189 (15), 175 (15), 168 (53), 154 (18), 143 (31), 127 (12), 115 (12), 84 (17); HRMS (EI): m/z calculated for [M]+. (C$_{14}$H$_{14}$O$_4$N$_2$): 247.0954; found 274.0959.

Elemental analysis, calculated (C$_{14}$H$_{14}$O$_4$N$_2$): C, 61.31; H, 5.14; N, 10.21; found: C, 61.05H, 5.22; N, 10.09.

EXAMPLE 8

Examination of the cyclisation speed of the substrate S3 (2-allyl-2-(2-methylallyl) diethyl malonate) when the catalyst 1.II is used.

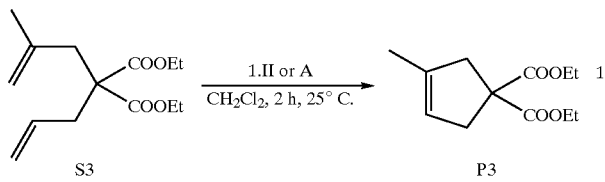

In a Schlenk tube a solution of diene S3 (100 mg, 0.4 mmol) in CH$_2$Cl$_2$ (20 ml) was placed at a temperature 25° C. a solution of the catalyst 1.II (2.6 mg, 0.004 mmol, 1 mol. %) in CH$_2$Cl$_2$ (1 ml) was added. The resulting mixture was stirred for additional 18 hours at the same temperature. Conversions were calculated from GC. (Aliquots of the reaction mixture were immediately quenched by addition of the calculated amount of 1 M solution of ethyl-vinyl ether and analysed by GC technique. Results obtained are presented on FIG. 1 as curve 10 (♦).

Examination of the cyclisation speed of the substrate S3 (2-allyl-2-(2-methylallyl) diethyl malonate) was repeated with catalyst A. Experiment was conducted under identical conditions as described above, except the amount of catalyst A was raised to 2.5 mol. %. Results obtained are presented on FIG. 1 as curve 2 (●).

EXAMPLE 9

Comparison of the efficiency of the catalysts 1.II and C in a cross metathesis reaction.

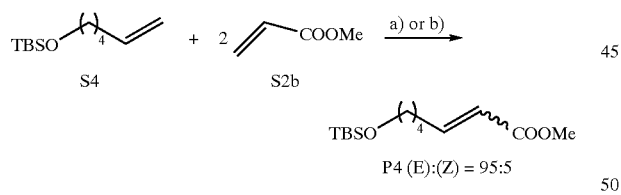

Condition a) Catalyst 1.II (1 Mol %), r.t., 30 min) yield 95%.

b) Catalyst C (2, 5 Mol %) r. t., 20 min) yield 91%.

To a stirred solution of olefin S4 (107 mg, 0.5 mmol) and methyl acrylate S2b (86 mg, 1 mmol) in CH$_2$Cl$_2$ (10 ml) solution of the catalyst 1.II (3.4 mg, 1 mol %) in CH$_2$Cl$_2$ (2 ml) was added. The resulting mixture was then stirred at room temperature for 30 min. Solvent was removed under reduced pressure and the residue was purified using silica-gel column chromatography (cyclohexane/EtOAc 8:2). The product P4 was obtained as a mixture of (E) and (Z)-isomers in the ratio 95:5 (130 mg, 95% of yield) as colourless oil.

According to the data in Angew. Chemie 2002, 114, 2509–2511 the catalyst of the formula C gives in an analogous reaction the product P4 with a yield of 91%.

EXAMPLE 10

Comparison of the efficacy of the catalyst 1.II and A in the cross metathesis reaction.

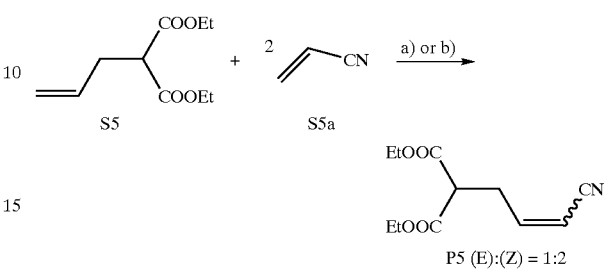

Condition a) Catalyst 1.II (5 Mol %), r. t., 30 min) yield 87%.

b) Catalyst A (8 Mol %) r. t., 6 h) yield 79%.

To a stirred solution of diethyl allylmalonate S5 (100 mg, 0.5 mmol) and S5a (53 mg, 1 mmol) in CH$_2$Cl$_2$ (5 ml) a solution of catalyst 1.II (16.8 mg, 5 mol %) in CH$_2$Cl$_2$ (5 ml) was added. The resulting solution was stirred at room temperature for 30 min. Solvent was removed under reduced pressure and the residue was purified using silica-gel column chromatography with (cyclohexane/EtOAc 8:2). Product P5 was obtained as a mixture of (E) and (Z)-isomers in the ratio 1:2 (98 mg, 87% of yield) as colourless oil.

According to Synlett 2001, 430–431, catalyst A gives an analogous reaction the product P5 with a yield of 79%.

I claim:

1. A compound of the formula 1,

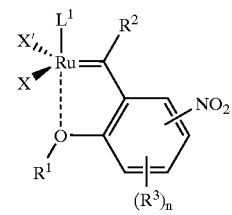

wherein

L$^1$ is a neutral ligand;

X and X' are anionic ligands;

R$^1$ is —C$_{1-5}$-alkyl or —C$_{5-6}$-cycloalkyl;

R$^2$ is H, —C$_{1-20}$-alkyl, —C$_{2-20}$-alkenyl, —C$_{2-20}$-alkynyl or aryl;

R$^3$ is —C$_{1-6}$-alkyl, —C$_{1-6}$-alkoxy or aryl, wherein aryl is optionally substituted with —C$_{1-6}$-alkyl or —C$_{1-6}$-alkoxy; and n is 0, 1, 2 or 3.

2. A compound according to claim 1 of the formula 1a,

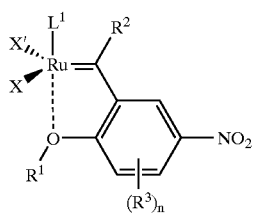
1a wherein $L^1$, X, X', $R^1$, $R^2$, $R^3$ and n are defined as in claim 1.

3. A compound according to claim 1, wherein
$L^1$ is $P(R^{11})_3$;
$R^{11}$ are each independently —$C_{1-6}$-alkyl, —$C_{3-8}$-cycloalkyl or aryl;
or $L^1$ is a ligand of formula 6a, 6b, 6c or 6d;

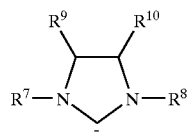
6a

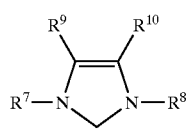
6b

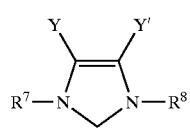
6c

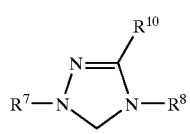
6d $R^7$ and $R^8$ are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen;
$R^9$ and $R^{10}$ are each independently H, —$C_{1-20}$-alkyl, —$C_{2-20}$-alkenyl or phenyl, wherein the phenyl is optionally substituted with up to three groups independently selected from —$C_{1-6}$-alkyl, —$C_{1-6}$-alkoxy or halogen; or
$R^9$ and $R^{10}$ together with the carbon atoms to which they are attached are combined to form an carbocyclic 3 to 8 membered ring;
Y and Y' are halogen.

4. A compound according to claim 3 wherein
$R^7$ and $R^8$ are each independently H, —$C_{1-6}$-alkyl, —$C_{2-6}$-alkenyl or phenyl, wherein the phenyl is optionally substituted with up to three groups independently selected from —$C_{1-6}$-alkyl, —$C_{1-6}$-alkoxy or halogen;
$R^9$ and $R^{10}$ are each independently H, —$C_{1-6}$-alkyl, —$C_{2-6}$-alkenyl or phenyl, wherein the phenyl is optionally substituted with up to three groups independently selected from —$C_{1-6}$-alkyl, —$C_{1-6}$-alkoxy or halogen; or
$R^9$ and $R^{10}$ together with the carbon atoms to which they are attached are combined to form an carbocyclic 5 to 7 membered ring.

5. A compound according to claim 1 wherein
$R^2$ is H, —$C_{1-6}$-alkyl or aryl; and
X and X' are halogen.

6. A compound according to claim 3 wherein
$L^1$ is $P(Cy)_3$ or a ligand of formula 6a, 6b, 6c or 6d;
Cy is cyclohexyl; and
X and X' are each chlorine.

7. A compound according to claim 3 wherein
$L^1$ is a ligand of formula 6a, 6b, 6c or 6d; and
$R^7$ and $R^8$ are 2-methylphenyl, 2,6-dimethylphenyl or 2,4,6-trimethylphenyl.

8. A compound according to claim 1 wherein
n is 0.

9. A compound according to claim 1 wherein
$R^1$ is isopropyl; and
$R^2$ is H.

10. A compound according to claim 1, wherein:
$R^1$ is isopropyl;
$R^2$ is H;
n is 0;
X and X' are each chlorine; and
$L^1$ is a ligand of formula 6a:

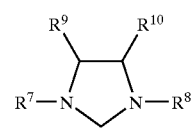
6a wherein $R^7$ and $R^8$ are each 2,4,6-trimethylphenyl; and
$R^9$ and $R^{10}$ are each H.

11. A compound according to claim 2, wherein:
$R^1$ is isopropyl;
$R^2$ is H;
n is 0;
X and X' are each chlorine; and
$L^1$ is a ligand of formula 6a:

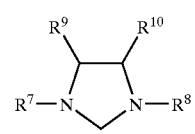
6a wherein $R^7$ and $R^8$ are each 2,4,6-trimethylphenyl; and
$R^9$ and $R^{10}$ are each H.

12. A compound of formula 2,

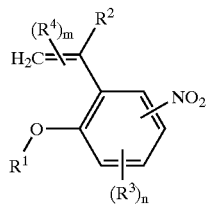

wherein
- $R^1$ is isopropyl;
- $R^2$ is H, $-C_{1-20}$-alkyl, $-C_{2-20}$-alkenyl, $-C_{2-20}$-alkynyl or aryl;
- $R^3$ is $-C_{1-6}$-alkyl, $-C_{1-6}$-alkoxy or aryl, wherein aryl is optionally substituted with $-C_{1-6}$-alkyl or $-C_{1-6}$-alkoxy;
- $R^4$ is $-C_{1-20}$-alkyl;
- m is 0, 1 or 2; and
- n is 0, 1, 2 or 3;

and wherein the partial formula:

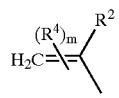

represents a group selected from the following:

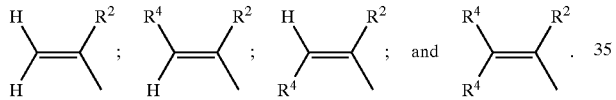

13. A compound according to claim 12 of formula 2a,

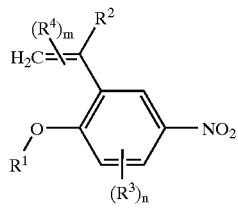

wherein $R^1$, $R^2$, $R^3$, $R^4$, m and n are defined as in claim 12;
and wherein the partial formula:

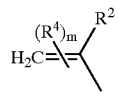

represents a group selected from the following:

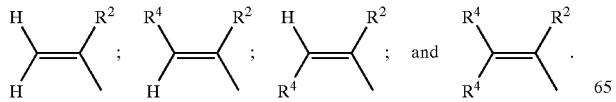

14. A compound according to claim 12 wherein
- $R^2$ is H, $-C_{1-6}$-alkyl or aryl;
- $R^4$ is $-C_{1-6}$-alkyl; and
- m is 0 or 1.

15. A compound according to claim 12 wherein
- $R^4$ methyl or ethyl; and
- n is 0.

16. A compound according to claim 12 wherein
- $R^1$ is isopropyl;
- $R^2$ is H;
- m is 0.

17. A compound of formula 2 according to claim 12, wherein:
- $R^1$ is isopropyl;
- $R^2$ is H;
- m is 0; and
- n is 0.

18. A compound of formula 2a according to claim 13, wherein:
- $R^1$ is isopropyl;
- $R^2$ is H;
- m is 0; and
- n is 0.

19. A process for manufacturing a compound of formula 1 according to claim 1, comprising:

(a) reacting a compound of formula 2:

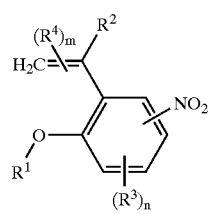

wherein
- $R^1$ is $-C_{1-5}$-alkyl or $-C_{5-6}$-cycloalkyl;
- $R^2$ is H, $-C_{1-20}$-alkyl, $-C_{2-20}$-alkenyl, $-C_{2-20}$-alkynyl or aryl;
- $R^3$ is $-C_{1-6}$-alkyl, $-C_{1-6}$-alkoxy or aryl, wherein aryl is optionally substituted with $-C_{1-6}$-alkyl or $-C_{1-6}$-alkoxy;
- $R^4$ is $-C_{1-20}$-alkyl;
- m is 0, 1 or 2; and
- n is 0, 1, 2 or 3;

and wherein the partial formula:

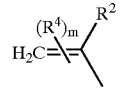

represents a group selected from the following:

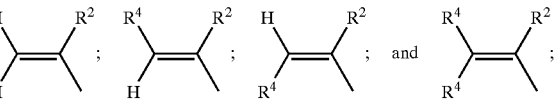

with a ruthenium complex of formula 5:

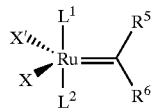

5 wherein

L¹ and L² are neutral ligands;
R⁵ is H, —$C_{1-20}$-alkyl, —$C_{2-20}$-alkenyl, —$C_{2-20}$-alkynyl or aryl;
R⁶ is aryl, vinyl or allenyl; and
X and X' are anionic ligands;
to obtain a compound of formula 1 according to claim 1; and (b) optionally reacting said compound of formula 1 obtained in step (a) with a different neutral ligand L¹ to replace the neutral ligand L¹ in said compound of formula 1 obtain a different compound of formula 1.

20. A process according to claim 19 wherein the process is carried out in the presence of a copper salt.

21. A process for manufacturing an intermediate of formula 2 according to claim 12, which process comprises the steps of:

a) alkylating a compound of formula 3,

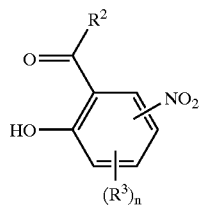

3 with a reagent of formula R¹Z (9) to form an intermediate of formula 4,

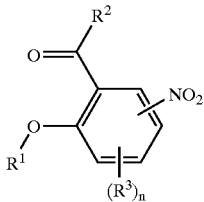

4 and
b) reacting the intermediate of formula 4 with an olefination reagent of formula 10;

10 to obtain a compound of formula 2:

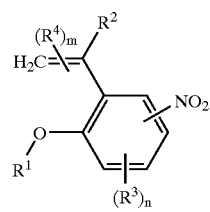

2 wherein R¹, R², R³, R⁴, m and n are as defined in claim 12;
and wherein the partial formula:

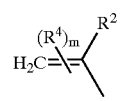

represents a group selected from the following:

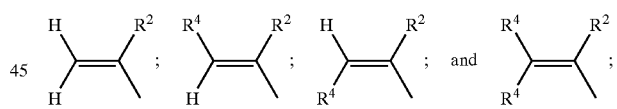

W is a leaving group suitable for olefination reactions; and
Z is halogen, $C_{1-6}$-alkyl-S(O)₂—, $C_{1-6}$-fluoroalkyl-S(O)₂—, aryl-S(O)₂— or aryl-S(O)₃—.

* * * * *